US00PP24627P3

(12) United States Plant Patent
Frazer

(10) Patent No.: US PP24,627 P3
(45) Date of Patent: Jul. 8, 2014

(54) ***DRACAENA* PLANT NAMED 'FUDRAFUT'**

(50) Latin Name: *Dracaena godseffiana*
Varietal Denomination: Fudrafut

(75) Inventor: Edwin Frazer, Brookfield (AU)

(73) Assignee: Florali Licensing B.V. (NL)

( * ) Notice: Subject to any disclaimer, the term of this patent is extended or adjusted under 35 U.S.C. 154(b) by 86 days.

(21) Appl. No.: 13/507,154

(22) Filed: Jun. 7, 2012

(65) Prior Publication Data

US 2013/0333086 P1 Dec. 12, 2013

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — Susan McCormick Ewoldt
(74) *Attorney, Agent, or Firm* — Cassandra Bright

(57) ABSTRACT

A new and distinct *Dracaena* cultivar named 'Fudrafut' is disclosed, characterized by distinctive variegated leaves, with dark green margins and lighter Yellow-Green colored interior. The new variety is a *Dracaena*, typically produced as an ornamental plant.

1 Drawing Sheet

Latin name of the genus and species: *Dracaena godseffiana.*

Variety denomination: 'Fudrafut'.

BACKGROUND OF THE INVENTION

The new cultivar is the product of induced mutation. The new variety originated as an induced mutation, by treating tissue cultured plantlets of an unnamed variety of *Dracaena godseffiana* with a known mutagen. The known chemical mutagen used was 10 ppm of 6 Benziylaminopurine.

The new variety was discovered by the inventor, Edwin John Frazer, a citizen of Australia, in 1995 in a commercial laboratory in Brookfield, Queensland, Australia. After identifying the new variety as a potentially interesting selection, the inventor continued selecting and propagating by tissue culture for several years until establishing a stable clone.

Asexual reproduction of the new cultivar 'Fudrafut' was first performed at the commercial laboratory in Brookfield, Queensland, Australia by meristem tissue culture. Access to all plants was restricted, as access to the laboratory was not open to the public. Through subsequent propagation by meristem tissue culture, multiple generations have been reproduced, which have shown that the unique features of this cultivar are stable and reproduced true to type.

SUMMARY OF THE INVENTION

The cultivar 'Fudrafut' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Fudrafut'. These characteristics in combination distinguish 'Fudrafut' as a new and distinct *Dracaena* cultivar:

1. Distinctive variegated leaves, with dark green margins and lighter Yellow-Green colored interior.

PARENT COMPARISON

Plants of the new cultivar 'Fudrafut' are similar to the parent, *Dracaena godseffiana* in most horticultural characteristics. The new variety, however, produces leaves with a distinct variegation, whereas the parent variety produces entirely green foliage.

COMMERCIAL COMPARISON

'Fudrafut' is in plant habit, and other horticultural characteristics most similar to the parent variety.

BRIEF DESCRIPTION OF THE PHOTOGRAPH

The accompanying photograph in FIG. 1 illustrates in full color a typical plant of 'Fudrafut' grown in a commercial greenhouse in Sint Oedenrode, The Netherlands. This plant is approximately 10 weeks old, shown planted in a 12 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Fudrafut' plants grown in a greenhouse in Honselersdijk, The Netherlands. Temperatures of approximately 18° to 20° C. at night and 20° to 22° C. during the day were maintained. No artificial light, photoperiodic treatments were given to the plants. Measurements and numerical values represent averages of typical plant types.

Botanical classification: *Dracaena godseffiana* 'Fudrafut'.

PROPAGATION

Time to initiate rooting: About 4 weeks at approximately 25° to 30° C. Full roots after 10-12 weeks. After 6 weeks temperature is lowered to normal values as described above.

Root description: Moderately thick, moderately fibrous, not fleshy, young roots white, near RHS 155A; older roots greyed-orange, near N170D.

PLANT

Age of plant described: Approximately 20 weeks from a fully rooted cutting.
Pot size of plant described: 12 cm pot.
Growth habit: Upright.
Height: Approximately 43.1 cm.
Plant spread: Approximately 34.7 cm.
Growth rate: Moderate, approximately 10 cm per month.
Branching characteristics: Not free branching, typically growing with one main stem from the base. Will only develop lateral branches after pinching.
Diameter of stem: Approximately 0.8 cm.
Internode length: Average 1.6 cm.
Texture of stem: Smooth, dull.
Color of stem: Near RHS N137A and 147A, axially striped lighter, near RHS 144C.
Stem strength: Very strong.
Number of leaves per stem: Average 19.

FOLIAGE

*Arrangement*.—Alternate (spirally).
*Average length*.—Approximately 17.4 cm.
*Average width*.—Approximately 6.3 cm.
*Shape of blade*.—Lorate.
*Aspect*.—Moderately curved downward.
*Apex*.—Apiculate.
*Base*.—Acuminate.
*Attachment*.—Sheathing.
*Margin*.—Entire.
*Texture of top surface*.—Smooth, moderately glossy.
*Texture of bottom surface*.—Smooth, moderately glossy.
*Color*.—Young foliage upper side: Near RHS 144A, irregular and conspicuously striped (axial) near 144C and N144A and N144B. Young foliage under side: Near RHS 144A, irregular and conspicuously striped (axial) near N144A and 150B. Mature foliage upper side: Near RHS N137A, irregular and conspicuously striped (axial) near 143A, 144A and 144B. Mature foliage under side: Near RHS 146B, irregular and conspicuously striped (axial) near 144B.
*Venation*.—Type: parallel. Color: Upperside: Indistinguishable from leaf blade. Underside: Main vein near RHS 145A and 145B, other veins colored as leaf blade.
*Sheath*.—Average Length: Approximately 1.6 cm. Average Width: Approximately 0.6 cm. Color: Near RHS 137C. Texture: Smooth, slightly glossy.

OTHER CHARACTERISTICS

Flower production: Not observed.
Disease resistance: Neither resistance nor susceptibility to normal diseases and pests of *Dracaena* has been observed.
Drought tolerance and temperature tolerance: Moderately high drought resistance, good heat resistance.
Fruit/seed production: Not observed.

What is claimed is:

1. A new and distinct cultivar of *Dracaena* plant named 'Fudrafut' as herein illustrated and described.

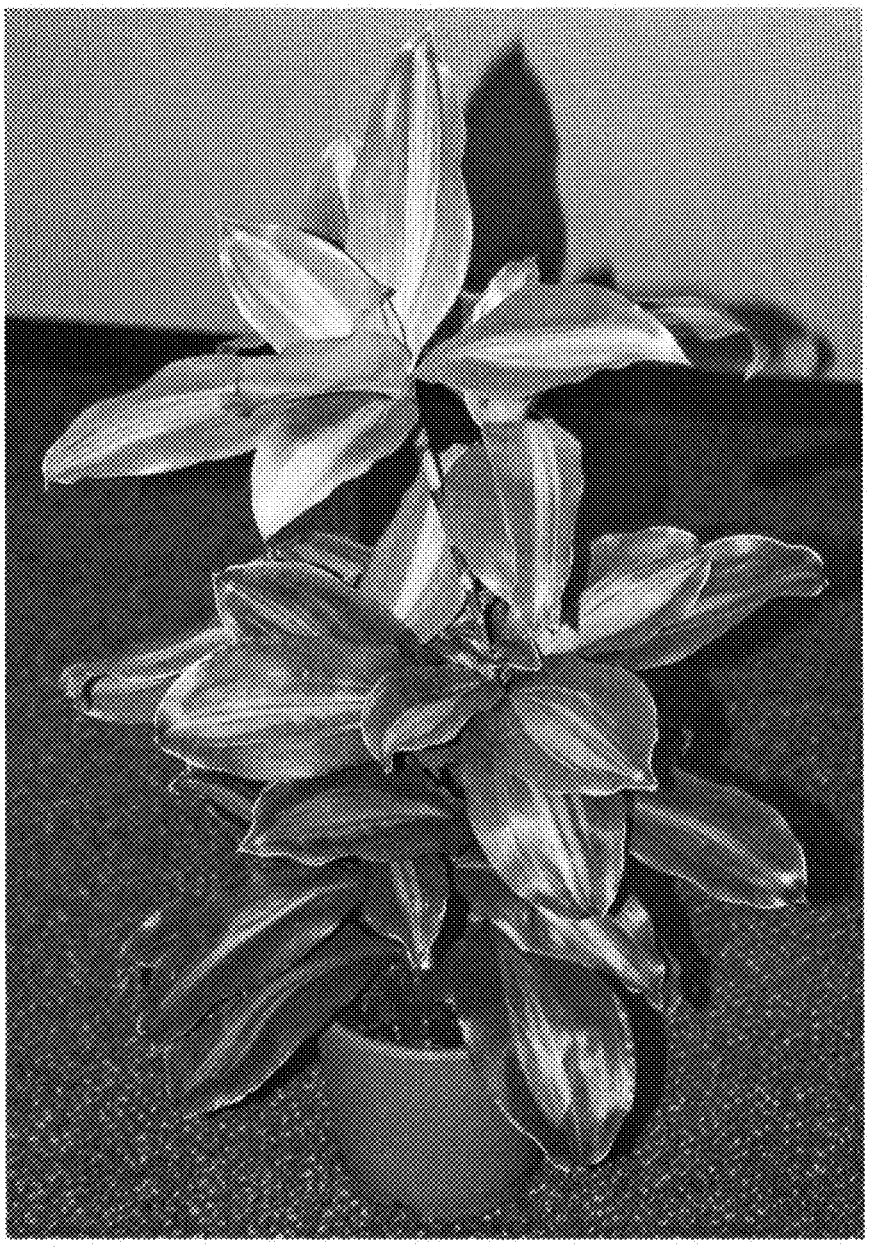

* * * * *